United States Patent [19]
Hirakawa et al.

[11] Patent Number: 5,814,581
[45] Date of Patent: Sep. 29, 1998

[54] PLANT GROWTH PROMOTER COMPRISING JASMONATE AND BRASSINOLIDE

[75] Inventors: Shin-ichi Hirakawa, Fujisawa; Yasuo Kamuro, Ichinomiya; Suguru Takatsuto, Joetsu; Tsuyoshi Watanabe, Atsugi; Hiroki Kuriyama, Kanagawa, all of Japan

[73] Assignee: Nippon Zeon Co., Ltd., Tokyo, Japan

[21] Appl. No.: 793,335

[22] PCT Filed: Aug. 25, 1995

[86] PCT No.: PCT/JP95/01693

§ 371 Date: Apr. 23, 1997

§ 102(e) Date: Apr. 23, 1997

[87] PCT Pub. No.: WO96/06529

PCT Pub. Date: Jul. 3, 1996

[30] Foreign Application Priority Data

Aug. 26, 1994 [JP] Japan .................................. 6-225674

[51] Int. Cl.⁶ .......................... A01N 37/02; A01N 37/06; A01N 43/22
[52] U.S. Cl. ........................................... 504/140
[58] Field of Search .............................. 504/140

[56] References Cited

PUBLICATIONS

Journal of Plant Growth Regulation (1994) 13:93–108, "Novel Natural Substances Acting in Plant Growth Regulation".

Sembbdner et al. "The biochemistry and the physiological and molecular actions of jasmonates". Ann. Rev.Plant Physiol. Plant Mol. Biol. 44:569–589, 1993.

Meudt, Werner. "Chemical and Biological Aspects of Brassinolide". Chapter 5 in Ecology and Metabolism of Plant Lipids. ACS Symposium Series No. 325. pp. 53–75, 1987.

*Primary Examiner*—S. Mark Clardy
*Attorney, Agent, or Firm*—Armstrong, Westerman, Hattori, McLeland & Naughton

[57] ABSTRACT

A plant growth promoter comprising as the active ingredients (i) a jasmonic acid or jasmonate of the formula (1):

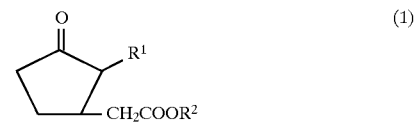

wherein $R^1$ is pentyl or pentenyl and $R^2$ is hydrogen or alkyl, and (ii) a brassinosteroid of the formula (2):

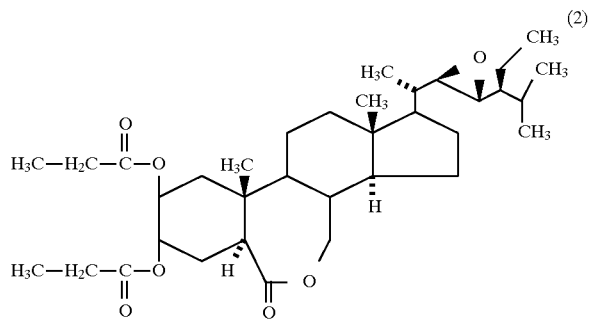

23 Claims, No Drawings

PLANT GROWTH PROMOTER COMPRISING JASMONATE AND BRASSINOLIDE

This application has been filed under 35 USC 371 as the national stage of International application PCT/JP95/01093, filed Aug. 25, 1995.

TECHNICAL FIELD

This invention relates to a plant growth promoter. More particularly, it relates to a plant growth promoter composition exhibiting growth-promoting effects for root-crops, potatoes and taroes, cereals, fruity vegetables, pulses, leafy vegetables, fruit-trees, woody plants, flowering plants, and industrial crops.

BACKGROUND ART

It has heretofore been a great problem in agricultural techniques to promote ordinary growth of crops and increase an agricultural production. It is expected that there will be a dearth of food in future in many lands on the globe, and the above-mentioned problem is becoming more important than ever. To solve this problem, many techniques have been proposed for controlling temperature and light irradiation in agricultural facilities, but special equipments or apparatuses are necessary, and the effects of growth promotion and production increase are not proportional to the labor expended.

In recent years, researches have been made on the actions of physiologically active substances isolated from vegetable tissues, which are exerted on the life environment of vegetables, i.e., on germination, growth, florescence, fructification and senescence, for the purpose of growth promotion and production increase. However, only a limited number of physiologically active substances exhibiting growth promotion of vegetables have heretofore been put to practical use, and only few active substances are practicable under the existing circumstances for the growth promotion in field cultivation.

DISCLOSURE OF INVENTION

A primary object of the present invention is to provide a plant growth promoter exhibiting an enhanced activity for the growth of plants.

After thorough research, the inventors have found that a combination of a jasmonic acid or jasmonate with a specific brassinosteroid compound exhibits an enhanced activity for plant growth-promotion, and thus, the present invention has been completed.

In accordance with the present invention, there is provided a plant growth promoter comprising as the active ingredient (i) a jasmonic acid or jasmonate represented by the following formula (1):

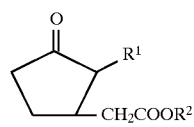

wherein $R^1$ is a pentyl or pentenyl group and $R^2$ is hydrogen or an alkyl group, and (ii) brassinosteroid represented by the following formula (2):

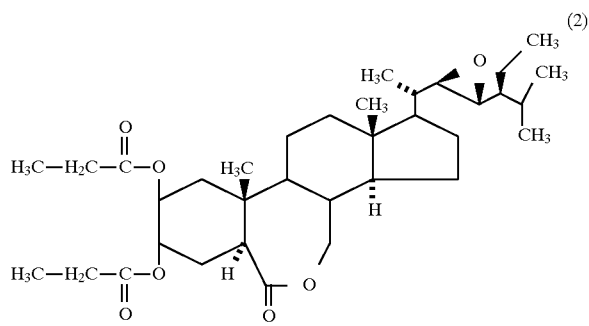

BEST MODE FOR CARRYING OUT THE INVENTION $R^1$ in the formula (1) represents a pentyl group or a pentenyl group. As the pentenyl group, a 2-pentenyl group is preferable. $R^2$ is a hydrogen atom or an alkyl group, and is preferably an alkyl group. The number of carbon atoms in the alkyl group is usually in the range of 1 to 10, preferably 2 to 6, and more preferably 3 or 4. As specific examples of the alkyl group, there can be mentioned methyl, ethyl, n-propyl, isopropyl, n-butyl, isobutyl, sec-butyl, t-butyl, n-pentyl, isopentyl, 2-methylbutyl, 1-methylbutyl, n-hexyl, isohexyl, 3-methylpentyl, 2-methylpentyl, 1-methyl-pentyl, n-heptyl, isoheptyl, n-octyl, isooctyl, 2-ethyl-hexyl, nonyl and decyl groups.

The jasmonic acid and jasmonate can be prepared by conventional methods. For example, a dihydrojasmonate, which has a pentyl group as $R^1$ in formula (1) and an alkyl group having 1 to 10 carbon atoms as $R^2$ in formula (1), can be prepared by allowing 2-pentylcyclopenten-1-one to react with an alkyl malonate by Michael addition, and then decarboxylating the thus-obtained reaction product.

Brassinosteroid of formula (2) is a known compound, and can be prepared by conventional methods. For example, a method can be employed wherein (22E, 24S)-24S-ethyl-5α-cholesta-2,22-dien-6-one is incorporated with N-methyl-morpholine-N-oxide and acetone; a catalytical amount of osmium tetraoxide is added to the mixture whereby the former compound is oxidized to give 2α,3α-dihydroxy-24S-ethyl-5α-cholest-22-en-6-one is obtained; the thus-obtained compound is allowed to react with propionic anhydride or propionyl chloride to give 2α,3α-dipropionyloxy-24S-ethyl-5α-cholest-22-en-6-one; and then the thus-obtained compound is allowed to react with an organic peracid such as m-chloroperbenzoic acid to give (22R,23R,24S)-2a,3a-dipropionyloxy-22,23-epoxy-B-homo-7-oxa-5α-stigmastan-6-one.

The ratio of the jasmonic acid or jasmonate of formula (1) to brassinosteroid of formula (2) in the plant growth promoter of the present invention is not particularly limited, and may be varied depending upon the particular crops, the intended purpose and the stage of development thereof. However, the ratio of brassinosteroid to the jasmonic acid or jasmonate is usually in the range of 1/0.1 to 1/1,000,000, preferably 1/1 to 1/100,000, and more preferably 1/10 to 1/10,000.

The plant growth promoter of the present invention can be applied either as it is or as a mixture with a carrier or, if desired, further with other adjuvants. The form of preparation thereof is not particularly limited, and may be a conventional form. For example, the active ingredients can be applied in the form of emulsions, suspensions, powders, hydrates, aqueous solutions, granules, pastes and aerosols.

If desired, the plant growth promoter of the present invention can be incorporated with conventional adjuvants such as a carrier, an emulsifier, a dispersant, a spreader, a wetting agent, an anchorage and a disintegrant.

As the carrier, solid carriers and liquid carriers are used. As preferable solid carriers used, there can be mentioned inorganic materials such as talc, bentonite, clay, kaolin, diatomaceous earth, white carbon, silicic anhydride, synthetic calcium carbonate, vermiculite, silica sand, mica, pumice, gypsum, calcium carbonate, dolomite, magnesium, calcium hydroxide, phosphorus lime, zeolite and ammonium sulfate; vegetable-based organic materials such as soybean powder, tobacco powder, walnut powder, wheat flour, wood flour, starch and crystalline cellulose; synthetic high polymeric substances and natural high polymeric substances such as cumarone resin, petroleum resin, alkyd resin, polyvinyl chloride, polyalkylene glycol, ketone resin, ester gum, copal gum and dammar gum; waxes such as carnauba wax and beeswax; and ureas. As preferable liquid carriers used, there can be mentioned paraffinic and naphthenic hydrocarbons such as kerosine, mineral oil, spindle oil and white oil; aromatic hydrocarbons such as benzene, toluene, xylene, ethylbenzene, cumene and methylnaphthalene; chlorohydrocarbons such as carbon tetrachloride, chloroform, trichloroethylene, monchloroethylene and o-chlorotoluene; ethers such as dioxane and tetrahydrofuran; ketones such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, ethanol, isopropanol, butanol, n-hexanol, ethylene glycol, propylene glycol and diethylene glycol; ether-alcohols such as ethylene glycol phenyl ether and diethylene glycol butyl ether, and polar solvents such as dimethylformamide and dimethylsulfoxide; and water.

As the emulsifier and the dispersant, surface active agents are usually used, which include nonionic, cationic, anionic and ampholytic surface active agents. In general a nonionic surface active agent and/or an anionic surface active agent is preferably used. As specific examples of the nonionic surface active agent, there can be mentioned products prepared by polymerizing and adding ethylene oxide to higher alcohols such as lauryl alcohol, stearyl alcohol and oleyl alcohol; products prepared by polymerizing and adding ethylene oxide to alkylphenols such as isooctyl phenol and nonyl phenol; products prepared by polymerizing and adding ethylene oxide to alkylnaphthols such as butylnaphthol and octylnaphthol; products prepared by polymerizing and adding ethylene oxide to higher fatty acids such as palmitic acid, stearic acid and oleic acid; products prepared by polymerizing and adding ethylene oxide to monoalkyl or dialkyl phosphates such as stearyl phosphate and dilauryl phosphate; products prepared by polymerizing and adding ethylene oxide to amines such as dodecylamine and stearic amide; higher fatty acid esters of a polyhydric alcohol such as sorbitan, and products prepared by polymerizing and adding ethylene oxide to the higher fatty acid esters; products prepared by addition-polymerization of ethylene oxide with propylene oxide; and esters of a polyvalent fatty acid with an alcohol, such as dioctyl succinate. As specific examples of the anionic surface active agent, there can be mentioned alkylsulfate salts such as sodium laurylsulfate and oleylsulfate amines; alkyl-sulfonate salts such as dioctyl sodium sulfosuccinate and 2-ethylhexyl sodium sulfonate; arylsulfonate salts such as sodium isopropylnaphthalenesulfonate, sodium methylenebisnaphthalenesulfonate, sodium ligninsulfonate and sodium dodecylbenzenesulfonate; and phosphate salts such as sodium tripolyphosphate.

The contents of the jasmonic acid or jasmonate and brassinosteroid in the plant growth promotor of the present invention may be varied depending upon the particular plant species, preparation form of the promotor, application procedure thereof and stage of plant development. When the plant growth promotor is applied in combination with a liquid carrier, i.e., as a solution, emulsion or suspension or other liquid preparation, the content of the jasmonic acid or jasmonate in the liquid preparation is usually in the range of 0.01 to 500 ppm, preferably 0.05 to 300 ppm, more preferably 0.1 to 200 ppm (weight/volume), and the content of brassinosteroid in the liquid preparation is usually in the range of 0.000001 to 1 ppm, preferably 0.0001 to 0.1 ppm, more preferably 0.001 to 0.01 ppm (weight/volume). Where the contents of the respective ingredients are within the specified ranges, the plant growth promoting effect develops efficiently.

When the plant growth promotor is applied in combination with a solid carrier, the content of the jasmonic acid or jasmonate in the solid preparation is usually in the range of 0.001 to 90% by weight, preferably 0.01 to 50% by weight, and the content of brassinosteroid in the solid preparation is usually in the range of 0.001 to 90% by weight, preferably 0.01 to 50% by weight, based on the total weight of the solid preparation.

A preferable procedure by which the plant growth promotor is applied varies depending upon the particular plant species and the object of application. For example, seeds, or potatos or taros are dipped in a liquid preparation, a liquid preparation is sprayed onto leaves and stems, the surface of leaves, flower bunches or fruits, a liquid preparation is injected into plants, or a liquid preparation is sprinkled on the soil. These application procedures can be employed alone or in combination. The application can be conducted at one time or several times.

The invention will now be described specifically by the following examples, but should not be construed to be limited thereto.

EXAMPLE 1

Growth-Promoting Effects by Treatment of Seeds of Wheat n-Propyl dihydrojasmonate (hereinafter abbreviated to "PDJ") and (22R,23R,24S)-2α,3α-dipropionyloxy-22,23-epoxy-B-homo-7-oxa-5α-stigmastan-6-one (hereinafter abbreviated to "BL") were incorporated in a mixed liquid composed of ethanol and water (volume ratio=50/50) to prepare a testing solution containing the active ingredients at concentrations shown in Table 1. Wheat seeds (variety: Norin #61) were flash-dipped in the test solution. The seeds were cultivated in a conventional manner. 100 plants were taken from each testing zone. Average individual live weight was measured, and the ratio in % of the live weight to that as measured on control plants cultivated without treatment with the active ingredient was calculated. The results are shown in Table 1. As seen from Table 1, synergistic growth-promoting effects are demonstrated by the combined use of PDJ with BL.

TABLE 1

| | Ratio of average individual live weight (%) | |
|---|---|---|
| PDJ (ppm) | BL: 0.01 ppm | BL: 0 ppm |
| 5 | 137 | 116 |
| 0 | 111 | 100 |

EXAMPLE 2

Growth-Promoting Effects by Spraying on Radish

PDJ was dispersed in a mixed liquid composed of xylol, isophorone and polyoxyethylene alkyl phenyl ether (volume ratio=60:20:20) to prepare a PDJ emulsion having a 20% (weight/volume) concentration. BL was dissolved in ethanol to prepare a BL solution having a 100 ppm concentration. Using the PDJ emulsion and the BL solution, aqueous testing solutions containing the active ingredients having concentrations shown in Table 2 were prepared.

Radish (variety: Akamaru-comet) was cultivated in a conventional manner in outdoor field, and, at the root hypertrophy initiating stage, the aqueous testing solutions were sprayed on the soil in an amount of 10 liters per are. Sixteen days after the spraying, 15 well grown individuals were harvested. The weights of the leaves and roots were measured, and the ratio in % of the weights to those as measured on control plants cultivated without application of the active ingredients were calculated. The results are shown in Table 2. As seen from Table 2, synergistic growth-promoting effects are demonstrated by the combined use of PDJ with BL.

TABLE 2

| | Ratio of leaf weight (%) | | Ratio of root weight (%) | |
|---|---|---|---|---|
| PDJ (ppm) | BL: 0.01 ppm | BL: 0 ppmL | BL: 0.01 ppm | BL: 0 ppm |
| 5 | 126 | 108 | 130 | 113 |
| 0.5 | 129 | 112 | 135 | 116 |
| 0 | 108 | 100 | 110 | 100 |

EXAMPLE 3

Growth-Promoting Effects by Treatment of Seed Potatoes

Testing solutions containing PDJ and BL at concentrations shown in Table 3 were prepared by using a mixed liquid composed of ethanol and water (volume ratio=70/30), and seed potatoes (May queen) were flash-dipped in the testing solutions.

Fifteen of the thus-dipped seed potatoes were planted in each zone of a field on the day after the dipping treatment, and cultivated in a conventional manner. Eighty days after the planting, 10 well grown plants were taken from each zone and weighed. From the average weights of potatoes, the ratio in % of the weight to that as measured on control potatoes cultivated without treatment with the active ingredient was calculated. The results are shown in Table 3. As seen from Table 3, synergistic growth-promoting effects are demonstrated by the combined use of PDJ with BL.

TABLE 3

| | Ratio of average potato weight (%) | |
|---|---|---|
| PDJ (ppm) | BL: 0.01 ppm | BL: 0 ppm |
| 50 | 138 | 113 |
| 0 | 109 | 100 |

EXAMPLE 4

Hypertrophic Growth-Promoting Effects on Tomato Fruit

By the same procedures as employed in Example 2, testing solutions containing either PDJ or BL or both thereof at concentrations shown in Table 4 were prepared. Tomatoes (variety: Momotarou) were conventionally cultivated inside a vinyl house in winter. The testing solutions were applied three times each in amount of 100 ml per individual. The first application was conducted at a stage of development wherein fruit hypertrophy of the tertiary fruit cluster was initiated and flowering of quaternary fruit cluster was terminated, the second application was conducted 20 days after the first application, and the third application was conducted one week before the harvest initiation of the tertiary fruit cluster, namely, 20 days after the second application.

All of the fruits of the tertiary fruit cluster and the quaternary fruit cluster were harvested in a conventional manner, and the fruits from each zone (10 plants per each zone) were weighed and the ratio in % of the average weight to that as measured on control tomatoes cultivated without application of the testing solutions was calculated. The results are shown in Table 4. As seen from Table 4, synergistic fruit growth-promoting effects are demonstrated by the combined use of PDJ with BL.

TABLE 4

| | Ratio of average fruit weight (%) | |
|---|---|---|
| PDJ (ppm) | BL: 0.01 ppm | BL: 0 ppm |
| 50 | 115 | 108 |
| 20 | 113 | 101 |
| 0 | 109 | 100 |

EXAMPLE 5

Low Temperature Injury-Preventing Effect

By the same procedures as employed in Example 2, testing solutions containing either PDJ or BL or both thereof at concentrations shown in Table 5 were prepared. Benjamin trees having an average height of 30 to 40 cm and 150 to 200 leaves were conventionally cultivated in pots within a green house. The testing solutions were sprayed onto each tree in an amount of 20 ml per tree. The treated trees were left to stand outdoors under natural low temperature conditions over a period of one month from the day after the application, spanning from the end of November to the end of December. The number of leaves fallen due to low temperature injury was counted. The defoliation ratio as defined by the following equation was determined.

Defoliation ratio (%)=(number of fallen leaves/−number of leaves before standing outdoors)×100 The results are shown in Table 5. As seen from Table 5, an enhanced low-temperature-injury-preventing effects are demonstrated by the combined use of PDJ with BL.

TABLE 5

| PDJ (ppm) | Ratio of defoliation (%) | |
| --- | --- | --- |
| | BL: 0.01 ppm | BL: 0 ppm |
| 30 | 16 | 31 |
| 0 | 38 | 94 |

EXAMPLE 6
Growth-Promoting Effect by Treatment of Paddy Rice Seeds

Paddy rice seeds (variety: Nippon-Bare) were immersed in cold water maintained at 15° C. for one day. By the same procedures as employed in Example 2, testing solutions containing either PDJ or BL or both thereof at concentrations shown in Table 6 were prepared. Then the seeds were immersed in each of the testing solutions for 24 hours, and further immersed in water for 3 hours. Then the thus-treated seeds were sowed in pots each having a diameter of 7 cm and cultivated at a temperature of 20° to 21° C. under continuously irradiated conditions at 15,000 lux in an air-conditioned room. When ¼ (i.e., 25%) of the control paddy rice plants cultivated in an untreated plant cultivation zone reached the trifoliate stage, the grown state (plant height and root live weight) of the rice plants of all cultivation zones was evaluated. The ratios in % of plant height and root live weight of the grown rice plants to those of the control rice plants cultivated in the untreated plant cultivation zone were calculated. The results are shown in Table 6.

TABLE 6

| PDJ (ppm) | Ratio of trifoliate plant (%) | | Plant height (%) | | Root live weight (%) | |
| --- | --- | --- | --- | --- | --- | --- |
| | BL: 0.01 ppm | BL: 0 ppm | BL: 0.01 ppm | BL: 0 ppm | BL: 0.01 ppm | BL: 0 ppm |
| 0.01 | 80 | 52 | 118 | 109 | 119 | 106 |
| 0 | 54 | 25 | 110 | 100 | 110 | 100 |

EXAMPLE 7
Growth-Promoting Effects by Treatment of Corn Seeds and Soybean Seeds By the same procedures as employed in Example 1, testing solutions containing either PDJ or BL or both thereof at concentrations shown in Table 7 were prepared. Seeds (soybean: honey bantam, soybean: mug-bean) were flash-dipped in each of the testing solutions and immediately then air-dried. The dried seeds were sowed at the conventional cultivating stage under field conditions. Twenty-five days after the sowing, the live weight of plants was measured, and the ratio in % of the live weight to that of control plants cultivated in an untreated seed-sowed zone. As seen from Table 7, a high growth-promoting effect can be achieved by the combined use of the two active ingredients.

TABLE 7

| PDJ (ppm) | Ratio of corn live weight (%) | | Ratio of soybean live weight (%) | |
| --- | --- | --- | --- | --- |
| | BL: 0.01 ppm | BL: 0 ppmL | BL: 0.01 ppm | BL: 0 ppm |
| 1 | 131 | 123 | 112 | 106 |
| 0.1 | 112 | 106 | 109 | 104 |
| 0 | 107 | 100 | 105 | 100 |

EXAMPLE 8
Yield-Increasing Effect by Spraying onto Paddy Rice Seedling

By the same procedures as described in Example 2, testing solutions containing either PDJ or BL or both thereof at concentrations shown in Table 8 were prepared. The testing solutions were sprayed onto paddy rice seedlings (variety: Chiyonishiki) in an amount of 150 ml per area of 25 cm×50 cm. Two days after the spraying, the seedlings were planted in a paddy field and conventionally cultivated. As seen from Table 8, the yield of unhulled rice is increased by the treatment with PDJ or BL alone, but it is much increased by the treatment with the combination of PDJ with BL.

TABLE 8

| PDJ (ppm) | Yield of unhulled rice (kg/are) | |
| --- | --- | --- |
| | BL: 0.01 ppm | BL: 0 ppm |
| 1 | 64 | 57 |
| 0 | 58 | 53 |

EXAMPLE 9
Effect of Enhancing Fruit Setting Rate of Peach

By the same procedures as employed in Example 2, testing solutions containing the active ingredients at the concentrations shown in Table 9 were prepared. Peach-trees (Hakuhou) were cultivated conventionally in a field. At the flowering initiating stage, each testing solution was sprayed in an amount of 300 liters per 10 ares, and, one month later, the fruit setting rate (i.e., the ratio of the number of fruits to the number of flowers upon spraying) was evaluated. As seen from Table 9, the combined use of PDJ with BL exhibits an enhanced fruit setting rate.

TABLE 9

| PDJ (ppm) | Fruit setting rate (%) | |
| --- | --- | --- |
| | BL: 0.01 ppm | BL: 0 ppm |
| 10 | 24 | 16 |
| 0 | 18 | 13 |

Industrial Applicability

The plant growth promotor of the present invention has a growth promoting effect on a wide variety of plants which include root-crops, potatoes and taroes, cereals, fruity vegetables, leafy vegetables, fruit-trees, woody plants, flowering plants and industrial plants. As specific examples of the plants to which the plant growth promotor is applied, there can be mentioned root-crops such as radish, carrot, onion, table beet, turnip and edible burdock; potatoes and taroes such as potatoes, sweat potato, taro and cassava; cereals such as rice, barley, wheat, oat, foxtail millet, barnyard millet, millet, buckwheat and corn; fruity vegetables such as cucumber, egg plant, sweet pepper, pumpkin, watermelon, oriental pickling melon, melon, musk melon, okra, strawberry and tomato; beans such as snap bean, broad bean, pea, soybean, peanut and azuki bean; leafy vegetables such as Chinese cabbage, cabbage, leek, cauliflower, parsley, Japanese hornwort, celery, crown daisy, spinach, lettuce, rape and potherb mustard; fruit-trees such as grape, pear, apple, peach, persimmon and mandarin orange; wood plants such as Japanese cedar, cypress, pine and hiba arborvitae; flowering plants such as lily, tulip, gladiolus, carnation and rose; and industrial crops such as cotton, hemp, sugar beet, turf and stevia. The plants to which the plant growth promoter is applied are not limited to these recited plants. For example, the plant growth promotor of the present invention can be used for grasses and trees as grown or planted in a desert or waste land.

Parts of plant systems at which the desired growth promoting effects of the plant growth promotor of the present invention are manifested vary depending upon the particular kind of plants. For example, the desired growth promoting responses develop on leaves, stems, roots, tubers, rhizomes, fruits and flower buds. More specifically, growth-promoting effects are manifested on leaves, stems, roots, tubers, rhizomes and fruits. Promotion of differentiation of flower puds is manifested, which leads to enhancement of germination rate and increase of the number of flowers. As regards fruits, setting rate, weight, degree of sweetness and color depth of fruits are enhanced.

We claim:

1. A plant growth promoter comprising as the active ingredients (i) a jasmonic acid or jasmonate, represented by the following formula (1):

wherein $R^1$ is a pentyl or pentenyl group and $R^2$ is hydrogen or an alkyl group, and (ii) a brassinosteroid represented by the following formula (2):

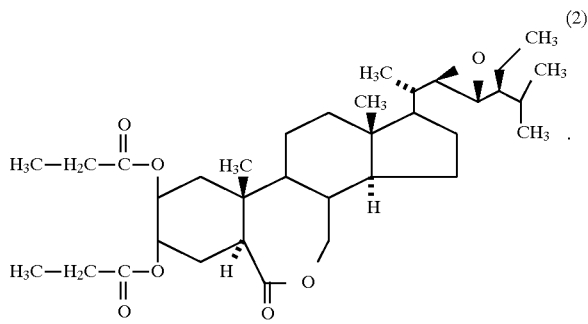

2. The plant growth promoter according to claim 1 wherein the ratio by weight of the brassinosteroid of formula (2) to the jasmonic acid or jasmonate of formula (1) is in the range of 1/0.1 to 1/1,000,000.

3. The plant growth promoter according to claim 1 wherein the ratio by weight of the brassinosteroid of formula (2) to the jasmonic acid or jasmonate of formula (1) to is in the range of 1/1 to 1/100,000.

4. The plant growth promoter according to claim 1 wherein $R^1$ in formula (1) is a pentyl group or a 2-pentenyl group.

5. The plant growth promoter according to claim 1 wherein $R^2$ in formula (1) is an alkyl group having 1 to 10 carbon atoms.

6. The plant growth promoter according to claim 1 wherein the jasmonate of formula (1) is n-propyl dihydrojasmonate.

7. The plant growth promoter according to claim 1 which further comprises a liquid carrier, and the contents of the jasmonic acid or jasmonate of formula (1) and the brassinosteroid of formula (2) are 0.01 to 500 ppm and 0.000001 to 1 ppm, respectively, based on the total weight of the plant growth promoter.

8. The plant growth promoter according to claim 1 which further comprises a solid carrier, and the contents of the jasmonic acid or jasmonate of formula (1) and the brassinosteroid of formula (2) are 0.001 to 90% by weight and 0.001 to 90% by weight, respectively, based on the total weight of the plant growth promoter.

9. A method of promoting plant growth which comprises applying to a plant a synergistically effective amount of the plant growth promoter of claim 1.

10. The method of claim 9, wherein the ratio by weight of the brassinosteroid to the jasmonic acid or jasmonate is in the range of 1/0.1 to 1/1,000,000.

11. The method of claim 9, wherein the ratio by weight of the brassinosteroid to the jasmonic acid or jasmonate is in the range of 1/1 to 1/100,000.

12. The method of claim 9, wherein the ratio by weight of the brassinosteroid to the jasmonic acid or jasmonate is in the range of 1/10 to 1/10,000.

13. The method of claim 9, wherein the plant is rootcrops, potatoes, taroes, cereals, fruity vegetables, pulses, leafy vegetables, fruit trees, woody plants, flowering plants, or industrial crops.

14. The method of claim 11, wherein potatoes and taroes are dipped in a liquid preparation comprising the plant growth promoter.

15. The method of claim 9, wherein a liquid preparation comprising the plant growth promoter is injected into the plant.

16. The method of claim 9, wherein a liquid preparation comprising the plant growth promoter is sprayed on a plant growth medium.

17. A method of promoting plant growth which comprises contacting a portion of a plant with a synergistically effective amount of the plant growth promoter of claim 1.

18. The method of claim 17, wherein the ratio by weight of the brassinosteroid to the jasmonic acid or jasmonate is in the range of 1/0.1 to 1/1,000,000.

19. The method claim 17, wherein the ratio by weight of the brassinosteroid to the jasmonic acid or jasmonate is in the range of 1/1 to 1/100,000.

20. The method of claim 17, wherein the ratio by weight of the brassinosteroid to the jasmonic acid or jasmonate is in the range of 1/10 to 1/10,000.

21. The method of claim 17, wherein the plant is rootcrops, potatoes, taroes, cereals, fruity vegetables, pulses, leafy vegetables, fruit trees, woody plants, flowering plants, or industrial crops.

22. The method of claim 17, wherein said portion of the plant is leaves, stems, roots, tubers, rhizomes, fruits, or flower buds.

23. The plant growth promoter of claim 1, wherein said plant growth promoter promotes the growth of root crops, potatoes, taroes, cereals, fruity vegetables, pulses, leafy vegetables, fruit trees, woody plants, flowering plants, or industrial crops.

* * * * *

UNITED STATES PATENT AND TRADEMARK OFFICE
CERTIFICATE OF CORRECTION

PATENT : 5,814,581

DATED : September 29, 1998

INVENTOR(S) : Hirakawa et al.

It is certified that error appears in the above-identified patent and that said Letters Patent is hereby corrected as shown below:

On the title page, under item [73] Assignee add the following:
-- and Tama Biochemical Co., both of Tokyo Japan Signed and Sealed this Nineteenth Day of October, 1999

Attest:

Q. TODD DICKINSON

Attesting Officer

Acting Commissioner of Patents and Trademarks